United States Patent [19]

Sinkora

[11] Patent Number: 4,573,919
[45] Date of Patent: Mar. 4, 1986

[54] DENTURE STABILIZER FOR MUSICIAN

[76] Inventor: Frank Sinkora, 7875 French St., Northfield, Ohio 44067

[21] Appl. No.: 606,381

[22] Filed: May 2, 1984

[51] Int. Cl.<sup>4</sup> ............................................. A61C 5/00
[52] U.S. Cl. ................................................... 433/140
[58] Field of Search .................. 433/138, 139, 140, 93

[56] References Cited

U.S. PATENT DOCUMENTS 2,172,998  9/1939  Grout et al. .................. 433/140
3,722,101  3/1973  Via ................................ 433/140

Primary Examiner—Robert Peshock
Attorney, Agent, or Firm—D. Peter Hochberg

[57] ABSTRACT

A denture stabilizer for musicians comprising of a spacer contoured to engage the musician's teeth extending from opposite jaws to hold a denture in place against the force of the mouthpiece of a musical instrument.

7 Claims, 6 Drawing Figures

DENTURE STABILIZER FOR MUSICIAN

BACKGROUND OF THE INVENTION

This invention relates to a device for enabling musicians wearing dentures to play musical instruments having mouthpieces against which the musician must press his mouth to play the instrument, and in particular, the brass wind instruments such as the trumpet, horn, trombone and tuba.

Players of the foregoing type of instruments press their lips against the mouthpiece of the instrument and blow air through the mouthpiece in order to obtain the desired sound. This act of playing the instruments also puts considerable force on the musician's teeth. Musicians with natural teeth have no problem coping with the forces applied against the teeth, but this is not the case for musicians wearing dentures. In fact, musicians wearing dentures have generally been required to abandon the brass wind instruments because their dentures tend to shift, slip and tilt as they press their lips against the mouthpiece of the respective instruments. This problem with dentures has caused amateur musicians to abandon the instruments causing a loss of satisfaction achieved from this musical endeavor, and has additionally caused economic loss to professional musicians whose wearing of dentures has required them to give up the playing of brass wind instruments and the like. There have heretofore been no known aids for enabling denture-wearing musicians to enable them to play musical instruments which involve the application of considerable force to their teeth.

SUMMARY OF THE INVENTION

It is an object of the present invention to enable musicians who wear dentures to play wind instruments which require the application of force to the dentures in the course of playing the instrument.

It is another object of the invention to provide a device for stabilizing the dentures of musicians when they play brass wind instruments and other instruments requiring the application of force to the dentures. It is a further object of the invention to provide a device of the foregoing type which is efficient and economical to manufacture and use, and easy to use.

Other objects will be apparent from the description to follow and from the appended claims.

The foregoing objects are achieved by the provision of a spacer which the musician clamps by mouth pressure between his opposing dentures or between natural teeth and dentures to stabilize and hold the dentures in place, while the instrument is played by the musician.

BRIEF DESCRIPTION OF THE DRAWINGS

FIGS. 3 and 4 are perspective views showing the upper and interior surfaces, respectively, of a second embodiment of the invention.

DESCRIPTION OF THE PREFERRED EMBODIMENTS

Figure 1:
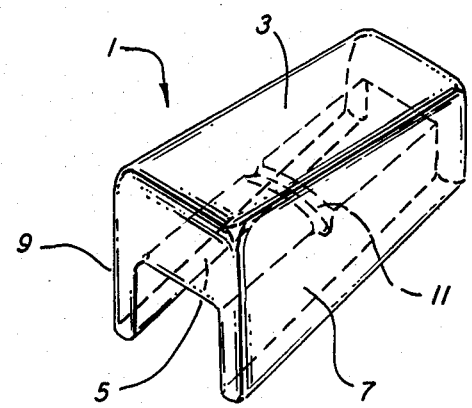
FIG. 1 is a perspective view of a denture stabilizer according to a preferred embodiment of the invention.

Referring to the drawings, FIG. 1 shows a denture stabilizer 1 which is a unitary plastic member having an upper surface 3, a lower surface 5 opposite the upper surface, and a pair of spaced, opposing side walls 7 and 9. Upper surface 3 has a generally centrally located longitudinal ridge configured for engagement with the working surfaces of several teeth extending from a musician's upper jaw. Lower surface 5 is configured to engage the working surfaces of teeth extending upwardly from a musician's lower jaw. The configuration of the lower surface preferably includes a transverse ridge 11 corresponding to the space between the wearer's teeth. Side walls 7 and 9 are configured to engage the sides of the teeth engaging surfaces 3 and 5, the ridge 11 preferably extending at least partially downwardly along the inner surfaces of side walls 7 and 9.

Figure 2:
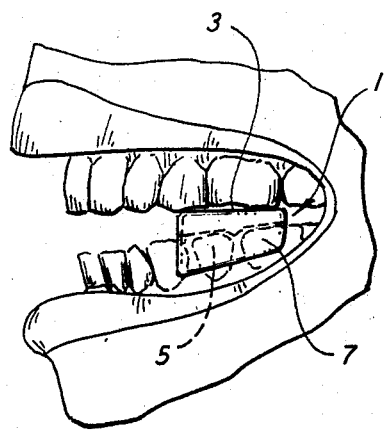
FIG. 2 is the side view of a musician showing the device of FIG. 1 clamped between the musician's dentures or natural teeth and dentures.
Figure 3:
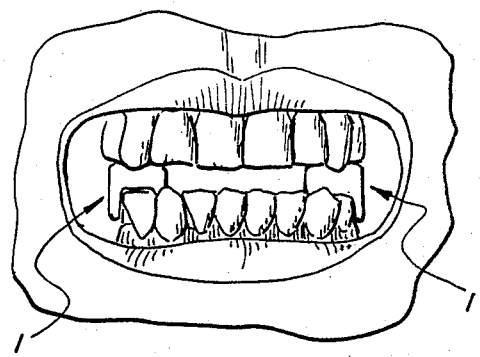
FIG. 3 is a front view of a musician having a pair of denture stabilizers as shown in FIG. 1, secured between his upper and lower jaws.
Figure 4:
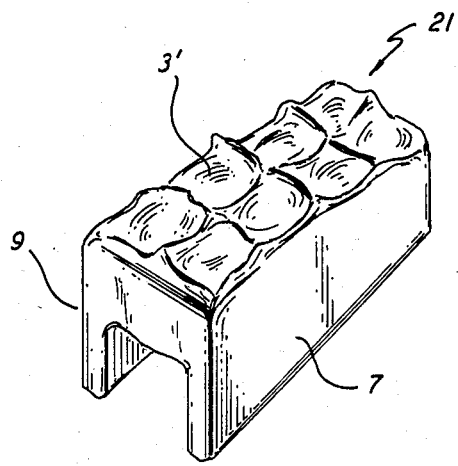
Figure 5:
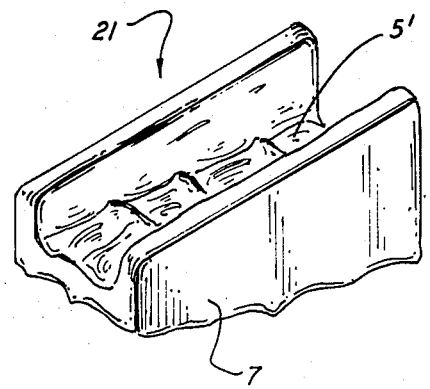
FIGS. 5 and 6 are side and front views, respectively, of a musician wearing a device according to the second embodiment of the invention.
Figure 7:
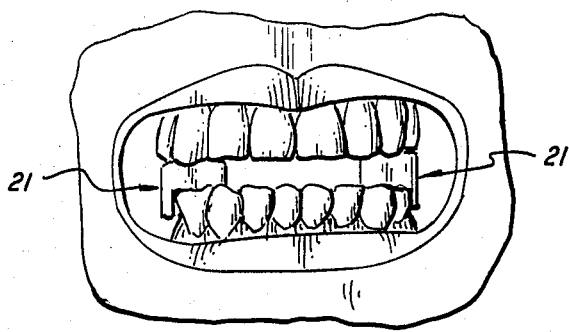
Figure 6:
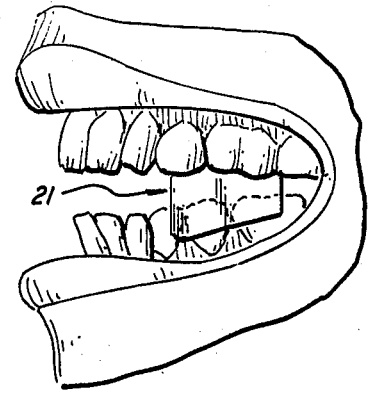

The manner of using the foregoing denture stabilizer is shown in FIGS. 2 and 3. FIG. 2, which shows one or a pair of stabilizers, indicates that the musician bites down on the stabilizer so that the working surfaces of the teeth extending downwardly from the upper jaw engage surface 3 of the stabilizer, while working surfaces of the teeth extending upwardly from the lower jaw engage lower working surface 5 of the stabilizer. Side wall 7 extends over and engages the outer side surfaces of the teeth extending from the lower jaw whose working surfaces engage surface 5 of the stabilizer. It can be seen from FIG. 2 that the stabilizer preferably has a length sufficient to span two molars.

Since most male adults who wear dentures wear the same general size, one universal size or perhaps a few sizes could be standardized for their use. Likewise, a similar size system could be used for women and children of different ages.

Some-denture wearing musicians, especially professional musicians, may have a need for a more effective stabilizer according to the invention. Accordingly, custom made denture stabilizers such as stabilizer 21 in FIGS. 4-7 would be appropriate. This stabilizer is also a unitary plastic member having side walls 7 and 9 as in the previous embodiment. However, the upper surface 3' is custom contoured to the wearer's teeth which engage that surface, while lower surface 5' is similarly contoured to the wearer's teeth which engage that surface. Custom made denture stabilizers according to this second embodiment of the invention can be made using techniques used in dentistry for making dentures, replacement teeth, crowns and the like. The stabilizers are preferably made of a strong, hygenic and durable plastic such as nylon. As noted, they are preferably molded, although other techniques such as machining are also available.

In use, the musician simply inserts one or two denture stabilizers according to the invention between the second and third opposing molars on one or both sides of the jaw, and bites down to clamp the stabilizer in place and hold the denture in place as well. Thereafter, the musician can press the mouthpiece of the instrument he wishes to play against his teeth without fear of tipping, turning, pushing or forcing the denture out of place.

Denture stabilizers according to the present invention are extremely effective in use and inexpensive to manufacture. They are far more effective than the denture paste which was the only device available in the past for assisting denture-wearing musicians in their efforts to play brass wind instruments, and should make it possible for frustrated brass wind instrument musicians to resume their musical activities with these instruments.

The invention has been described in detail with particular emphasis on the preferred embodiment thereof, but it should be understood that variations and modifications may occur to those skilled in the art to which it pertains.

We claim:

1. A denture stabilizer for musicians comprising a member having a flattened upper surface for engagement by the teeth extending from the musician's upper jaw and a flattened lower surface opposite said upper surface for engagement by the teeth extending from the musician's lower jaw, said upper and lower surfaces being spaced from each other by a distance small enough to maintain the musician's mouth in a substantially closed position, and one of said upper and lower surfaces having an irregular contour to engage the irregular surface of the teeth engaged by said surface, said stabilizer holding a denture comprising any said teeth in the musician's mouth in place against forces applied to the denture by the mouthpiece of a musical instrument.

2. The invention according to claim 1 wherein said upper surface is configured to receive in a mating relationship the lower surfaces of the teeth by which it is engaged.

3. The invention according to claim 1 wherein said lower surface is configured to receive in a mating relationship the upper surfaces of the teeth by which it is engaged.

4. The invention according to claim 1 wherein said stabilizer further includes a side wall for engaging the outer side surfaces of the teeth.

5. The invention according to claim 1 and further including a side wall for engaging the inner side surfaces of the teeth.

6. The invention according to claim 1 wherein the stabilizer is a unitary piece of plastic.

7. The invention according to claim 1 wherein the stabilizer is made of rigid plastic.

* * * * *